United States Patent [19]

Harrison

[11] 4,365,622
[45] Dec. 28, 1982

[54] MULTIPLE PLATE RESONANT ELECTRODE

[75] Inventor: William H. Harrison, Woodland Hills, Calif.

[73] Assignee: Donald L. Morton & Associates, Los Angeles, Calif.

[21] Appl. No.: 186,391

[22] Filed: Sep. 11, 1980

[51] Int. Cl.³ .............................................. A61N 1/42
[52] U.S. Cl. ................................... 128/1.3; 128/804; 219/10.79
[58] Field of Search ................................... 128/1.3–1.5, 128/783, 802, 804; 219/10.79; 336/232

[56] References Cited

U.S. PATENT DOCUMENTS

| | | | |
|---|---|---|---|
| 2,847,651 | 8/1958 | Schamanek | 219/10.79 X |
| 2,939,049 | 5/1960 | Blackman | 219/10.79 X |
| 3,256,417 | 6/1966 | Merrett | 219/10.79 |
| 3,824,729 | 2/1958 | Emerson et al. | 219/10.79 X |
| 4,207,451 | 6/1980 | Tudbury | 219/10.79 |

Primary Examiner—Lee S. Cohen
Attorney, Agent, or Firm—Poms, Smith, Lande & Rose

[57] ABSTRACT

A self-resonant single-turn electrode for use in the treatment of animal tissue with hyperthermia by coupling the electrode to a supply of radio frequency energy. The electrode comprises a plurality of planar annular disc members concentrically stacked with dielectric material therebetween. Each disc has a radial slit therethrough to form a gap. The discs are stacked with the gaps of adjacent discs 180° apart. The radio frequency energy may be coupled to the entire stack by connecting to only one disc and the discs are all insulated from each other.

3 Claims, 8 Drawing Figures

4,365,622

MULTIPLE PLATE RESONANT ELECTRODE

BACKGROUND OF THE INVENTION

The present invention relates to apparatus for the treatment of animal tissue by hyperthermia and, more particularly, to a self-resonant single-turn electrode for use with such equipment.

In my U.S. Pat. No. 4,186,729, a deep heating electrode and method of use thereof for the treatment of animal tissue through hyperthermia is shown. Such an electrode is basically a self-resonant single-turn loop which, when attached to a source of radio frequency energy, produces concentric lines of substantially equal energy within the space defined by the electrode such that when animal tissue is placed therein the tissue is equally heated throughout. This approach allows deep heating within a human body in contrast to the conventional diathermy approach which results in high energy consumption with attendant high heating by the subcutaneous fat layers and very little energy transfer with attendant heating in the deeper regions where such heating is desired.

An improvement to the basic teachings of the above mentioned patent is shown in my co-pending U.S. patent application Ser. No. 97,485 entitled Planar Disc Magnetic Electrode, now abandoned, wherein a flattened disc electrode is shown for the particular purpose of creating a flat energy region for use in such areas as the neck where it is not desired to have energy also being transmitted to the head and brain while treatment is being conducted on the neck region.

One embodiment according to the general teaching of the above mentioned co-pending application is shown in FIGS. 1 and 2. The RF path length around the disc represents the inductive portion of the resonant circuit while the overlapping segment provides a capacitor which, in conjunction with the inductor, forms a resonant circuit.

In a tested embodiment of the prior art disc of FIG. 1, the large electrically conductive disc 10 is annular, having an inside dimension of 10 inches, and an outside dimension of 20 inches. Disc 10 has a radial slit 12 therethrough, forming a gap therein. A second electrically conductive disc 14 of similar radial dimensions but extending only over one half the first disc 10 (i.e. a semi-annular) is concentrically placed over the opening of the first disc 10 and equally across the gap of slit 12. When the discs 10, 14 are separated by a 0.030 inch Teflon sheet of dielectric material 16, a capacity of approximately 1700 pf is obtained and the resonant frequency is approximately 13.6 Mhz.

FIG. 3 shows the equivalent circuit and illustrates that the total capacity measured between plates (electrically conductive discs 10, 14) is distributed on either side of the inductance of the circuit. Thus, one-half of that total value is placed on each side of the gap (i.e. radial slit 12). In effect, the two halfs are in series with each other and are across the inductor with respect to the resonant circuit. Therefore, the effect of capacity across the gap is one-fourth of the total capacity measured with a low frequency bridge. This has been verified by measurements of the capacity and the circuit resonant frequency.

For other areas of the body requiring treatment, such as the hand or foot, the dimensions of the disc must be significantly reduced to properly couple energy into that extremity of the body. The reduced disc dimensions cause the RF path length to be reduced, and the resulting inductance is proportionately diminished. Thus, the capacity needed to resonate the circuit at the same frequency is greatly increased.

The capacity produced by overlapping plates is directly proportional to their area and is inversely proportional to the dielectric thickness. With a smaller electrode disc, the available area is reduced and there is also a voltage breakdown consideration which limits the minimum thickness of the dielectric material. Thus, as dimensions are reduced, a point is reached where it becomes impossible to resonate the electrode with completely overlapping plates.

The conventional approach to stacking a plurality of capacitor plates is shown in FIG. 4. A typical, well known, example of such multi-plate capacitors is a tuning capacitor. Alternate plates 18 are electrically interconnected and tied to electrical leads 20. In this type of arrangement, the total capacity $C_T = C_1 + C_2 + C_3 + C_4 + C_5$.

Wherefore, it is the object of the present invention to provide a planar disc electrode capable of being made in a small size and made self-resonant through the use of stacked plates which do not necessarily require interconnection.

It is a further object of the present invention to provide a planar disc electrode with stacked plates which is easily adjustable as to the amount of capacity contained therein so as to allow the electrode to be placed in a self-resonant state at the desired frequency.

SUMMARY

The foregoing objectives have been realized in the self-resonant single-turn electrode of the present invention comprising a plurality of planar members of electrically conductive material shaped in the form of annular discs. The annular discs each have a single slit radially therethrough to form a gap. The discs are stacked concentrically in non-electrical contact with dielectric material therebetween and with the gap of each of the discs disposed 180° from the next adjacent one of the discs. Only one of the discs has means for operative attachment to a supply of radio frequency energy, thereby providing inductive coupling to the complete stack of discs.

DESCRIPTION OF THE PREFERRED EMBODIMENT

Figure 4:
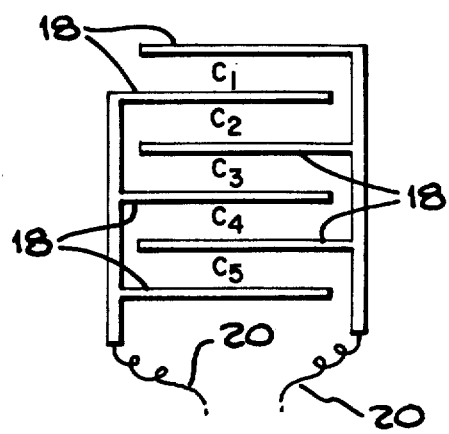
FIG. 4 is a simplified drawing of a multi-plate stacked capacitor according to prior art.
Figure 5:
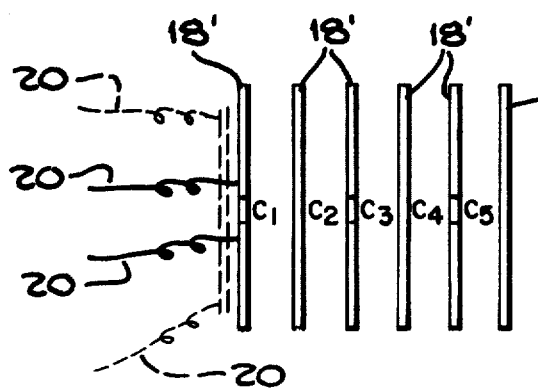
FIG. 5 is a simplified drawing of the principle of operation of the electrode of the present invention.

The present invention employs non-contacting, multiple, electrically conductive capacitor plates with the construction thereof differing significantly from the typical known multi-plate capacitor as, for example, the one shown in FIG. 4. The construction of the present invention is shown in simplified form in FIG. 5. Therein, a plurality of plates 18' are separated and stacked in close adjacent spaced relationship but in non-electrical contact. Plates 18' are annular and have a gap 12 disposed 180° apart in alternate places. RF energy is connected across the gap 12 of one plate 18' as with wires 20 connected thereto or inductively with a separate inductive loop (ghosted 21) disposed concentrically close-spaced thereto. A capacitive potential, therefore, exists between each adjacent pair of plates 18' labeled, as with the capacitor of FIG. 4, as $C_1$, $C_2$, $C_3$, $C_4$ and $C_5$. Only the first plates 18' bounding capacitor potential $C_1$ have electrical leads 20 connected thereto. As will be seen, the electrical capacitive characteristics of FIG. 5 and FIG. 4 will be identical. That is, the total capacity $C_T$ is equal to the sum of the individual capacitors. That is, $C_1+C_2+C_3+C_4+C_5$.

Figure 1:
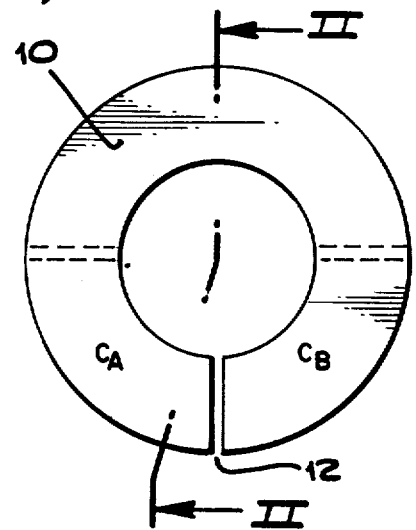
FIG. 1 is a front elevation view of a planar disc electrode according to prior art.
Figure 2:
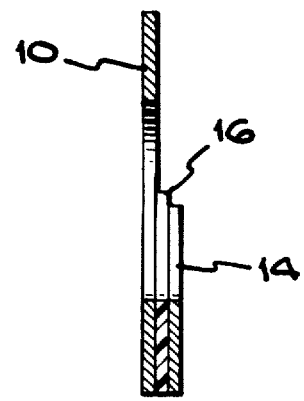
FIG. 2 is a cut-away side elevation of the electrode of FIG. 1 in the plane II—II.
Figure 3:
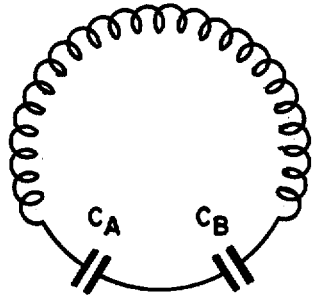
FIG. 3 is a drawing of the electrical equivalent circuit of the electrode of the FIGS. 1 and 2.
Figure 6:
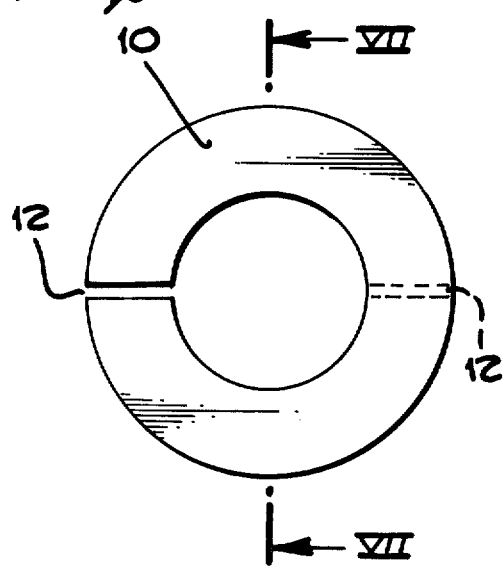
FIG. 6 is a front elevation view of the electrode according to the present invention.
Figure 7:
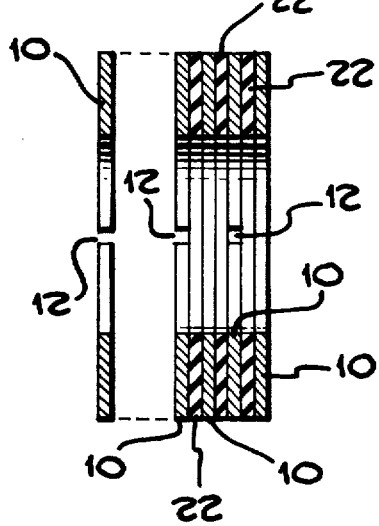
FIG. 7 is a side cut-away view through the electrode of FIG. 6 in the plane VII—VII.

The exact mode of constructing the electrode of the present invention is shown in FIGS. 6 and 7. A plurality of annular discs 10 of the type shown in FIG. 1 having a radial slit 12 therein are employed. Whereas the electrode of the prior art embodiment used only one such disc 10, the present invention uses a plurality of identical discs having annular sheets of dielectric material 22 concentrically disposed therebetween. To achieve the desired results, the slits 12 are placed 180° apart and adjacent discs 10. Note that the discs 10 of electrically conductive material are not electrically interconnected one to another. It should also be noted that if the discs 10 were not configured and positioned to become part of an inductor as well as being the plates of a capacitor, the individual plate capacities ($C_1$, $C_2$, etc.) would be in series rather than in parallel. By being an integral part of inductance, however, they are placed in parallel as necessary to achieve the desired objectives.

This construction technique is very desirable and is a simplifying feature in the construction of the electrode of the present invention since it eliminates special tabs on each capacitor plate and, also, no means of electrically tying the plates together is needed. From a physical point of view, the plates (discs 10) are thus completely independent and can be readily added or removed to adjust the resonant frequency of the completed electrode.

In a tested embodiment of the electrode of FIGS. 6 and 7, the dielectric material 22 is 0.009 inch Teflon brand material. The individual discs have an inside diameter of 2.25 inches and an outside diameter of 4.25 inches being made of 0.025 inch aluminum sheet. This configuration provided 616 pf of measured capacity between adjacent plates. A resonant electrode was built up one plate at a time with the initial inter-plate capacity and the resonant frequency being measured as each plate was being added.

The electrical characteristics of the electrode of the present invention can be considered as follows. Since the capacity is distributed on both sides of the gap (radial slit 12) and the two halfs are in series, the effective capacity across the inductance formed by the circuit is $616 \div 4 = 154$ pf. The measured resonant frequency with the two plates is 43.5 Mhz which establishes an inductance of 0.087 uHy. It should be pointed out once again that the identical inductance/capacitance plates (discs 10) are rotated so that the gap (slit 12) is always the opposite of the adjacent plate. This must be done to place the capacities in parallel and across the inductance.

Circuit parameters of 0.087 uHy, 616 pf and a resonant frequency of 43.5 Mhz (while using two plates) establishes that the capacity must be increased by a factor of 10.29 to reduce the resonant frequency to the 13.56 Mhz. medical frequency desired. Thus, approximately 10 additional capacities equal to the initial capacity between the two plates are required (i.e. a total of 11 plates).

Figure 8:
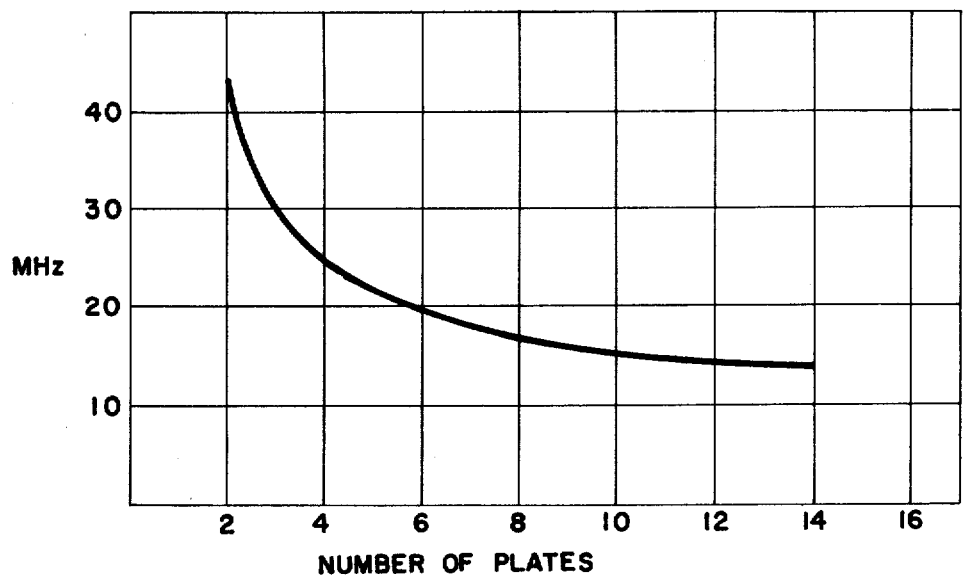
FIG. 8 is graph showing the resonant frequency of a tested embodiment of the present invention as a function of the number of plates employed therein.

A plot of the electrode resonant frequency versus the number of stacked non-contacting plates is shown in FIG. 8. As may be seen, eleven plates produced a resonant frequency of 15.7 Mhz, and actually fourteen plates were required to resonate at 13.9 Mhz. This increased number of plates is attributed to a slight lowering of the inductance. As plates are added, the resonator thickness is increased from its initial 0.059 inches to a final value of 0.477 inches. The inductance is thus reduced from 0.087 uHy. to approximately 0.065 uHy. This is theoretically anticipated.

If the sizes of the individual discs 10 and the thickness/material of the dielectrical material 22 were changed, of course, a different individual capacitance and inductance would be obtained.

As can be seen, the construction of the present invention allows a multi-plate electrode to be constructed having exactly the right number of plates to place it in resonance at the desired frequency without the necessity for electrically connecting the multi-plates together. Having thus being "tuned", the electrode is self-resonant at exactly the proper frequency such that there is virtually no chance of its being detuned as in the case of an adjustable electrode having a variable capacitor associated therewith, while, at the same time, providing maximum energy transfer.

Wherefore, having thus described my invention, I claim:

1. A self-resonant single-turn electrode for use in the treatment of animal tissue by hyperthermia by coupling the electrode to a supply of radio frequency energy, the electrode comprising:
    a plurality of planar members of electrically conductive material shaped in the form of annular discs, said annular discs each having a single slit radially therethrough to form a gap, said discs being stacked concentrically and insulated from one another with dielectric material disposed therebetween, said gap of each of said discs being disposed 180° from the next adjacent ones of said discs, one of said discs having means associated therewith for operative attachment to a supply of radio frequency energy.

2. The electrode of claim 1 wherein:
    said operative attachment means comprises means for connecting a pair of wires directly to said one of said discs across said gap thereof.

3. The electrode of claim 1 wherein:
    said operative attachment means comprises a separate inductive loop for connection to the energy supply disposed in concentric, parallel, close-spaced relationship to said one of said discs.

* * * * *